United States Patent [19]

Bonsen et al.

[11] 4,001,200

[45] * Jan. 4, 1977

[54] NOVEL POLYMERIZED, CROSS-LINKED, STROMAL-FREE HEMOGLOBIN

[75] Inventors: Pieter Bonsen, Los Altos, Calif.; Myron B. Laver, Weston, Mass.; Kent C. Morris, Mountain View, Calif.

[73] Assignee: Alza Corporation, Palo Alto, Calif.

[ * ] Notice: The portion of the term of this patent subsequent to Jan. 4, 1994, has been disclaimed.

[22] Filed: Feb. 27, 1975

[21] Appl. No.: 554,051

[52] U.S. Cl. .................. 260/112.5 R; 260/112 B; 424/177
[51] Int. Cl.$^2$ ............... C07C 103/52; A61K 37/00
[58] Field of Search ............... 260/112.5 R, 112 B; 424/177

[56] References Cited

UNITED STATES PATENTS 3,057,782   10/1962   Lindner et al. .................. 424/177

OTHER PUBLICATIONS

Fasold et al.: Angew. Chem. Internat. Ed., 10, 795–801 (1971).
Wold; Methods in Enzymol., 11, 617–640 (1967).

*Primary Examiner*—Lewis Gotts
*Assistant Examiner*—Reginald J. Suyat
*Attorney, Agent, or Firm*—Paul L. Sabatine; Edward L. Mandell; Thomas E. Ciotti

[57] ABSTRACT

This invention concerns polymerized, cross-linked, stromal-free hemoglobin useful as a blood substitute for carrying oxygen to tissues and organs, as a blood plasma expander and for supplying oxygen to oxygen-requiring environments.

6 Claims, 10 Drawing Figures

NOVEL POLYMERIZED, CROSS-LINKED, STROMAL-FREE HEMOGLOBIN

CROSS-REFERENCE TO RELATED APPLICATION

This application is related to United States Patent Application Ser. No. 553,514, filed on Feb. 27, 1975. This application and the related application are assigned to the same assignee.

BACKGROUND OF THE INVENTION

1. Field of the Invention

The present invention relates to a novel and useful biological polymer polymerized, cross-linked, stromal-free hemoglobin. The polymerized hemoglobin has the property of reversibly binding gaseous ligands such as oxygen and is useful as a blood substitute for transporting and supplying oxygen to vital tissues and organs, as a blood plasma substitute, as a source of oxygen for biological systems, and for furnishing oxygen to oxygen-consuming environments.

2. Description of the Prior Art

Hemoglobin is present in the blood of mammals and it has the fundamental property in solution of reversible oxygenation. In its natural form, mammalian hemoglobin is a conjugated, non-crosslinked protein having a molecular weight of 64,500 and structurally comprised of two pairs of sub-units. Each sub-unit contains a heme group and a polypeptide chain, called globin. In mammals, hemoglobin is present in erythrocytes along with stroma which consists of proteins, phospholipids and cholesterol. *Clinical Hematology*, by Wintrobe, 6th Ed., pages 138 to 199, 1967, published by Lea and Febiger, Phildelphia, Pa. The reaction of isolated, bovine hemoglobin containing stroma with glutaraldehyde is known to the art in *Histochemical J.*, Vol. 2, pages 137 to 150, 1970, wherein Hopwood used an excess of glutaraldehyde to obtain an insoluble precipitate. Similarly, the reaction of whole blood proteins with glutaraldehyde leading to a water insoluble glue is disclosed by Karjala, et al in U.S. Pat. No. 3,294,564. The interaction of the collagen and collagen degradation product gelatin with diisocyanates and other polycoupling agents, including aldehydes, is reported by Campbell in U.S. Pat. No. 2,591,133, by Linder, et al, in U.S. Pat. No. 3,057,782, and by Bowes in *Biochemica et Biophysica Acta*, Vol. 168, pages 341 to 352, 1968. The carboxyalkylation of globin for use as a plasma expander is taught by Biddison in U.S. Pat. No. 2,719,837; however, the products obtained by the above reactions lacked the ability to transport oxygen and in consequence thereof, they did not enter into general use. In U.S. Pat. No. 2,527,210, Bower disclosed the use of hemoglobin for treating wounds, in U.S. Pat. Nos. 3,000,836 and 3,519,572, Ginsburg and Kita disclosed blood preparations having utility as standards for measuring hemoglobin, and in Nederland Pat. No. 7,404,140 cross-linked hemoglobin containing stroma having utility as a plasma substitute is disclosed.

SUMMARY OF THE INVENTION

This invention concerns polymerized, cross-linked, stromal-free hemoglobin. In this application, the terms "polymerized hemoglobin", "cross-linked, stromal-free hemoglobin", and "macro-molecular, stromal-free hemoglobin" are hereinafter referred to as "polyhemoglobin", and for this invention, these terms are deemed as equivalents. By polyhemoglobin is meant at least one stromal-free hemoglobin tetramer, $Hb_4$, cross-linked within the tetramer, or with at least one other heme containing stromal-free hemoglobin monomer, $Hb$, dimer, $Hb_2$, trimer, $Hb_3$, or tetramer, $Hb_4$, to yield the polymer of the general formula, $poly(Hb)_n$, wherein n is 4 to 60, preferably 8 to 30.

The polyhemoglobin of the invention is prepared from stromal-free mammalian hemoglobin which is cross-linked with a bifunctional or a polyfunctional cross-linking agent. The polyhemoglobin is soluble in aqueous fluids having a pH of 6 to 9 and in physiological fluids. The polyhemoglobin has a molecular weight of 64,000 to 1,000,000 and the property in solution of reversibly binding gaseous ligands in an amount up to 60 $\mu$ mol of ligand per gram of polyhemoglobin, that is, the oxygen-carrying capacity is close to 100%. The polyhemoglobin, depending on its preparation exhibits a partial oxygen pressure at half-saturation of 2.5 mm Hg to 120 mm Hg at 37° C, measured at neutral pH and atmospheric pressure. The polyhemoglobin solutions have an intrinsic viscosity of 0.04 to 0.16 deciliters per gram and exhibit ultraviolet and visible spectra similar to non-crosslinked hemoglobin. The polyhemoglobin, in the oxidized state when its heme iron is trivalent and the polyhemoglobin is cross-linked, stromal-free polymethemoglobin, has a molar extinction coefficient, $\epsilon$, at 630 nm equal to $3.5 \pm 0.4 \times 10^3$ in the absence of heme ligand, and a $\epsilon$ at 540 equal to $9.5 \pm 0.5 \times 10^3$ for cross-linked, stromal-free polycanomethemoglobin, polymethemoglobin with cyanide as the heme ligand.

DETAILED DESCRIPTION OF PREPARATION OF POLYHEMOGLOBIN

The polyhemoglobin is prepared starting with erythrocytes separated from freshly drawn human blood, from outdated whole blood, placentas or packed erythrocytes obtained from human donor centers, or from erythrocytes obtained from animal blood. The blood is drawn into bottles containing an anticoagulant, centrifuged, and the supernatant plasma withdrawn. Centrifuging is carried out at −5° C to 40° C, preferably at 4° C to 6° C, for about 5 to 60 minutes, and at 650 to 6500g, with the supernatant plasma and buffy coat removed and discarded. Next, the red cells are washed in about 1 to 4 volumes of cold, isotonic saline, or hypertonic sodium chloride, the suspension centifuged and the supernatant removed and discarded. The red cells are washed an additional 2 to 3 times, with the wash discarded after each centrifugation.

The method of obtaining the starting material for the polymerization, includes isolating hemoglobin from cells substantially free of cellular debris and stroma. The removal of stromal proteins and lipids is critical to the invention as its removal essentially eliminates renal damage as known to the prior art where hemoglobin solutions containing these were used as blood substitutes. The general procedure used herein for obtaining stromal-free hemoglobin includes first lysing the cells in about one to four volumes of cold water or other lysing solutions such as hypotonic phosphate buffers, or hypotonic saline. After lysing, the red cell suspension is shaken and cold toluene is added in about 10 to 200% of the cell volume, usually about 10 to 30% of the volume. The mixture is then shaken for 4 to 10 minutes and left standing at 4° C to 6° C for 24 to 72 hours to produce a triphasic mixture. The lower, clear red layer is isolated and centrifuged at 40,000 to 50,000g for at least 60 minutes at about 4° C to 6° C. Then, the upper clear supernatant is separated and filtered through a diatomaceous earth filter. This filtration removes any traces of stroma, and various precipitation tests can be used to ascertain if the hemoglobin is stromal-free. Suitable tests are described in *Hawk's Physiological Chemistry*, pages 181 to 183, 1965, published by McGraw-Hill Company. Similar methods for obtaining stromal-free hemoglobin are reported in Journal of *Experimental Medicine*, Vol. 126, pages 185 to 193, 1969; Annals of *Surgery*, Vol. 171, pages 615 to 622, 1970; *Haematologia*, Vol. 7, pages 339 to 346, 1973; and *Surgery*, Vol. 74, pages 198 to 203, 1973.

Residual low molecular weight salts and metabolites are removed from the stromal-free hemoglobin by dialysis against standard or medically acceptable buffers. Buffers suitable for the purpose include 0.05 M phosphate and physiological saline buffered with alkali bicarbonates. The stromal-free hemoglobin is dialyzed by using commercially available equipment such as a Dow miniplant using Biofiber - 50 dialysis fiber, the Kolff system using a semipermeable membrane or a Crom-A-Coil unit dialyzer. Semipermeable dialysis membranes operable for the purpose include cellulose, cellulose acetate, modified cellulose acetate membranes such as N,N-diethylamino ethylcellulose acetate and cellulose propionate.

The dialysis is carried out at 4° C to 6° C by passing stromal-free hemoglobin solution through hollow cellulosic fibers, with the hemoglobin dialyzed against a buffer passed along the outside of the fiber. Generally, the fibers have an exclusion limit that permits passage of low molecular weight solutes without egress of hemoglobin. The flow rate of fluid is greater than 1 ml per minutes, preferably 3 to 25 ml per minute. The stromal-free hemoglobin is passed through the fibers three times to establish equilibrium. Suitable dialysis methods are reported in *Methods of Enzymology*, Vol. XXII, pages 23 to 32, 1971, published by Academic Press, New York.

Next, the dialyzed hemoglobin is polymerized to form water soluble macro-molecular cross-linked, stromal-free hemoglobin. The stromal-free hemoglobin for cross-linking can be either liganded or unliganded hemoglobin corresponding to the presence or the absence of heme ligands. When either oxygen or carbon monoxide are present as the heme ligand, the hemoglobin is known as oxyhemoglobin and carbomonoxyhemoglobin, respectively. When there is no heme ligand present, the hemoglobin is deoxyhemoglobin. These hemoglobins are described in *Hawk's Physiological Chemistry*, pages 335 to 342, 928 to 940, and 1090 to 1099, published in 1965 by McGraw-Hill Book Company. The oxyhemoglobin and carbomonoxyhemoglobin are prepared by equilibration with the corresponding gases, oxygen or carbon monoxide, at a temperature of 4° to 6° C, for about 30 minutes to 60 minutes. Deoxyhemoglobin is prepared by repeated evacuation of the solution under decreased pressure, usually about 250 mm Hg, followed by flushing with nitrogen or an inert gas such as argon or neon. Deoxyhemoglobin can also be prepared by chemical deoxygenation with the addition of reducing agents such as sodium dithionite, or sodium sulfite. The presently preferred forms of hemoglobin for cross-linking with a cross-linking agent that produces a soluble polyhemoglobin, are oxyhemoglobin and deoxyhemoglobin. As it has now been found, cross-linking of these hemoglobins produces polyhemoglobins having a $P_{50}$ value of from 4 mm to 120 mm Hg at about physiological conditions, 37° C and pH 7.1, depending on the method of preparation of the polyhemoglobin. This range of $P_{50}$ values of 4 to 120 mm Hg includes the hemoglobin oxygen affinities as found in blood and free, naturally occurring hemoglobin.

The polymerization of dialyzed stromal-free hemoglobin is carried out by the intermolecular cross-linking of usually the primary amino groups of its lysine residues to yield water-soluble polyhemoglobin. The cross-linking is performed in the presence of at least one bi- or polyfunctional cross-linking agent to produce greater than 90% macro-molecular hemoglobin. The polymerization is carried out by first purging the reaction vessel with the appropriate gaseous ligand, such as oxygen for the synthesis of poly(oxy)hemoglobin; carbon monoxide for the preparation of poly(carbomonoxy)hemoglobin; and with an inert gas such as nitrogen, or argon, for the synthesis of Then, the hemoglobin is cross-linked under a blanket of the appropriate gas, that is, oxygen, carbon monoxide, argon, or nitrogen. The reaction is performed at a temperature of 0° to 25° C, from 3 hours to 300 hours, and at normal atmospheric pressure. Elevated pressures up to 5 atmospheres can also be used. Generally, about 1 equivalent of the reactant hemoglobin, having a molecular weight of 64,000, is reacted with 2.5 to 300 equivalents of the bi- or polyfunctional cross-linking reagent.

It is essential to the invention that the cross-linking agent used yield cross-linked hemoglobin soluble in aqueous and physiological media. This is achieved by using the agents described below. The formation of insoluble forms of polyhemoglobin can be prevented by adding about 5 to 30 equivalents of a low molecular weight amine to the hemoglobin solution before the addition of the cross-linking agent. The hemoglobin and cross-linking reagents are thoroughly mixed and allowed to react with constant stirring for about ¼ hours to 300 hours at 4° to 6° C. The reaction is terminated by quenching with from 100 to 500 equivalents of low molecular weight amine. High level thermal oxidation of hemoglobin is prevented by carrying out the reaction at low temperatures, usually 0° C to 10° C. Any increase in reaction temperature is accompanied by shorter reaction times. As the concentration of the cross-linking reactant is increased, the tendency for insoluble polymerization products to form can increase, and this is prevented by the addition of a low molecular weight amine, or a mixture of low molecular weight amines. The amount of amine added is an amount sufficient to react with the unreacted functional group of a cross-linking agent bound to a hemoglobin moiety, usually a stoichometric amount or an excess up to 250 equivalents of amine to one equivalent of cross-linking agent. Following addition of the quenching amine, the reaction is stirred an additional 18 to 24 hours at 4° C. The crude reaction mixture is clarified by centrifugation and dialyzed against an isotonic electrolyte solution. The soluble polyhemoglobin obtained is sterilized by filtering through a filter having a pore size of about 0.20 to 0.45 microns, preferably 0.22 microns.

The bi- or polyfunctional cross-linking agents suitable for the purpose of the invention are preferably water soluble, and reactive with cross-linkable sites of hemoglobin, to yield a cross-linked water soluble product. The cross-linking agents used do not adversely effect hemoglobin, its solubility, or its function of reversibly binding oxygen for supplying it to tissues and organs. The bi- or polyfunctional cross-linking agents have at least two functional groups, and they can be the same or different. These groups are capable of reacting with and cross-linking amino groups and other cross-linkable sites on the hemoglobin molecule. By amino groups is meant the N-terminal alpha amino group of the hemoglobin chains, and those of the basic amino acid residues such as lysine and arginine.

The functional groups of the cross-linking agent can be covalently bonded to each other or they can be separated by an aliphatic or by an aromatic ring. Exemplary aromatic stabilized functional groups are azo and halo activated with a nitro group. These include compounds having a heterocyclic ring with reactive groups bonded to the ring. For example, triazines of the formula:

wherein $R_1$ is halogen including fluoro, chloro and bromo, and $R_2$ is a nucleophilic substituent such as an aliphatic or aromatic group, a halogen, a lower alkyl of 1 to 8 carbons, and amino. Cross-linking agents embraced by this formula are 2-amino-4,6-dichloro-s-triazine and chloro-s-triazine. The cross-linking agents include aromatic stabilized agents prepared by the diazotation of an aromatic diamine, for example, benzidine and its derivatives with nitrous acid to yield bis-diazobenzidines of the formula:

wherein $R_3$ is a member selected from the group consisting of a covalent bond, alkylene of 1 to 5 carbons, phenylene, ether, sulfone and secamine, $R_4$ is halogen or nitro, $R_5$ is hydrogen, nitro, lower alkyl of 1 to 8 carbons, sulfonate ($SO_3H$) and carboxylate, and $R_6$ is halogen, diazo (-N:N-), isocyanate (NCO), and isothiocyanate (NCS). Representative agents embraced by the formula include bis-diazobenzidine 2,2'-sulfonic acid, 4,4'-difluoro-3,3'-dinitrophenylsulfone and diphenyl-4,4'-diisothiocyanate.

Cross-linking agents suitable for the invention include compounds of the formula:

wherein $R_7$ is halogen and $R_8$ is nitro, or hydrogen with at least one $R_8$ a nitro, as represented by the commercially available activated halogenated reagent 1,5-difluoro-2,4-dinitrobenzene.

Cross-linking agents suitable for the purpose of the invention also include compounds of the formula $(R_9)_2C = O$ wherein $R_9$ is hydrogen or halogen, and compounds of the formula $R_{10}-(CH_2)_n-R_{10}$ wherein $R_{10}$ is the same or different and $n$ is 1 to 8. The agents also include compounds having a functional group bound to an aromatic moiety either directly or through an alkylene bridge of the formula $R_{10}-(CH_2)_m-C_6H_4-(CH_2)_m-R_{10}$ wherein $R_{10}$ is the same or different and $m$ is 0 to 3. Cross-linking agents include the compounds having the functional groups bonded to a cycloalkyl as represented by the formula:

wherein $R_{10}$ is the same or different, $p$ is 0 to 4, and $q$ is 1 to 4. The cross-linking agents include compounds having functional groups bonded to an aliphatic chain interrupted with a nonfunctional group or having nonfunctional groups bonded to the chain as represented by compounds of the formula $R_{10}-(CH_2)_x-R_{11}-(CH_2)_x-R_{10}$ wherein $R_{10}$ is the same or different, $R_{11}$ is selected from the group consisting of an ether bridge, a divalent amine and a sulfone, and $x$ is an alkylene of 1 to 5 carbon atoms, with each $x$ the same or different. Representative of the functional group embraced by $R_{10}$ include isocyanate, vinyl, imine, isothiocyanate, isocyanide, aldehyde, epoxide, chloroformate, thiochloroformate, and imido lower alkyl ester, and thiolactones of the formula:

wherein $a$ is 1 to 3. Also, $R_{10}$ can be an activated group formed by reacting the carboxylic acid with a thionyl halide or phosphorus halide, or an activated group formed by reacting an amide or an alkyl ester of the carboxylic acid with hydrazine and then with nitrous acid to yield the corresponding activated group $COR_{12}$ wherein $R_{12}$ is halogen or azide. The activated group can also be formed by reacting the carboxylic acid with N,N'-carbonyl diimidazole of the formula $R_{13}-N=C=N-R_{13}$ wherein $R_{13}$ is the same or different and are a lower alkyl, a lower cycloalkyl, amino lower alkylene, and heterocyclic lower alkyl including morpholino ethyl. $R_{12}$ can also be a lower alkyl, and a wherein $n$ is 1 or 2.

Exemplary commercially available cross-linking reagents embraced by the above formula include divinyl sulfone, epichlorohydrin, butadiene diepoxide, ethylene glycol diglycidyl ether, glycerol diglycidyl ether, dimethyl suberimidate dihydrochloride, dimethyl malonimidate dihydrochloride, and dimethyl adipimidate dihydrochloride.

Representative of compounds bearing a functional isocyanate or isothiocyanate group are the compounds listed below. Additionally, the isocyanates or isothiocyanates can be synthesized by reacting an alkyl or aryl amine with phosgene or thiophosgene. The isocyanates used for cross-linking are diisocyanates and they react with the free amino groups of hemoglobin producing urea or thiourea cross-linked sites. Typical compounds include diphenyl-4,4'-diisothiocyanate-2,2'-disulfonic acid, toluene diisocyanate, toluene-2-isocyanate-4-isothiocyanate, 3-methoxydiphenylmethane-4,4'-diisocyanate, propylene diisocyanate, butylene diisocyanate, and hexamethylene diisocyanate.

Exemplary of cross-linking agents having an aldehyde or dialdehyde functionality include formaldehyde, paraformaldehyde, formaldehyde activated ureas such as 1,3-bis(hydroxymethyl)urea, N,N'-di(hydroxymethyl) imidazolidinone prepared from formaldehyde condensation with a urea according to the formula $CH_2O + R_{16}HN-CO-NHR_{16} \rightarrow HOCH_2NR_{16}-CO-NR_{16}-CH_2OH$ wherein $R_{16}$ is hydrogen, alkyl, aryl or heterocyclic ring. Other dialdehyde cross-linking agents include dialdehydes of the formula $OCH-R_{17}-HCO$ wherein $R_{17}$ is a member selected from the group consisting of a covalent bond and a straight or branched chain alkylene of 1 to 8 carbons. Dialdehydes embraced by the formula include gloxal, malonic dialdehyde, succinic dialdehyde, glutaraldehyde, adipaldehyde, 3-methyl glutaraldehyde, propyladipaldehyde, phthalic dialdehyde, terephthaldehyde and malonic dialdehyde.

Other cross-linking agents include derivatives of carboxylic acids and carboxylic acid residues of hemoglobin activated in situ to give a reactive derivative of hemoglobin that will cross-link with the amines of another hemoglobin. Typical carboxylic acids useful for this purpose have the formula $CO_2H(CH_2)_nCO_2H$, and $\{(CH_2)_nCOOH\}_3CH$ wherein $n$ is 1 to 8. The carboxylic acids include citric, malonic, adipic and succinic. Carboxylic acid activators include thionyl chloride, carbodiimides, N-ethyl-5-phenyl-isoxazolium-3'-sulphonate (Woodward's reagent K), N,N'-carbonyldiimidazole, N-t-butyl-5-methylisoxazolium perchlorate (Woodward's reagent L), 1-ethyl-3-dimethyl aminopropylcarbodiimde, 1-cyclohexyl-3-(2-morpholinoethyl) carbodiimide metho-p-toluene sulfonate. The cross-linking reaction using a carboxylic acid can be represented by the equation $RCO_2H \xrightarrow{activator} RCOX \xrightarrow{Hb-NH_2} RCONH-Hb$.

Other cross-linking groups that can be used are prepared from esters and thioesters activated by strained thiolactones, hydroxysuccinimide esters, halogenated carboxylic acid esters and imidates. The above functional reagents or methods for preparing them are reported in *Bull. Soc. Chem. Fr.*, Vol. 12, pages 4613 to 4617, 1971; *Biochemical Aspects of Reactions on Solid Supports*, by Stark, George R., Chapter 1, published by Academic Press, 1971; *Chemtech*, pages 47 to 55, 1974; *Rev. Pure and Appl. Chem.*, Vol. 21, pages 83 to 113, 1971; and British Pat. No. 1,252,770.

The cross-linking reagent can be a dialdehyde precursor that readily forms a bifunctional dialdehyde in the reaction medium. Suitable dialdehyde precursors include acrolein dimer or 3,4-dihydro-1,2-pyran-2-carboxaldehyde which undergoes ring cleavage in an aqueous environment to give alpha-hydroxy-adipaldehyde. Other precursors, which on hydrolysis yield a cross-linking reagent, include 2-ethoxy-3,4-dihydro-1,2-pyran which gives glutaraldehyde, 2-ethoxy-4-methyl-3,4-dihydro-1,2-pyran which yields 3-methyl glutaraldehyde, 2,5-diethoxy tetrahydrofuran which yields succinic dialdehyde and 1,1,3,3-tetraethoxypropane which yields malonic dialdehyde and formaldehyde from trioxane. The above bifunctional reagents are known in *Beilstein's Handbook*, Vol. 7, Suppl. 1, page 12; ibid, Vol. 1, Suppl. 2, page 12; ibid, Vol. 1, Suppl. 2, page 831; ibid, Vol. 1, Suppl. 3, page 3076; ibid Vol. 1, Suppl. 2, page 824; and ibid, Vol. 1, Suppl. 2, page 572. Similarly, the cross-linking reagents can be prepared by known synthetic procedures such as malonaldehyde from tetraethyl acetal, succinaldehyde from diethoxytetrahydrofuran, and adipaldehyde by the oxidation of cyclohexanediol.

In the above formula, the expression "an alkylene of 1 to 8 carbons" includes straight or branched chain alkylenes such as methylene, ethylene, propylene, isopropylene and hexylene. The expression "lower alkyl of 1 to 8 carbons" includes straight or branched chain alkyls such as methyl, ethyl, propyl, isopropyl, and hexyl.

The low molecular weight amine added to the polymerization vessel for regulating the cross-linking reaction, or for quenching it, is a mono-, di-, or multifunctional agent, preferably a primary amine of the formula $R-NH_2$. The amine should be water soluble to assist in maintaining the solubility characteristics for the polymerized hemoglobin. Typical low molecular weight amines used to deactivate excess cross-linking agents are glycine, lysine, serine, threonine, alanine, ethanolamine, 2-aminoadipic acid and glutathione. Other compounds capable of deactivating the cross-linking agents are terminators such as bisulfites and diols capable of deactivating aldehydes, low molecular weight alcohols for deactivating activated carboxylic acids, activated halides and isocyanates, and sulfhydryls for deactivating epoxides and vinyls.

The following examples are set forth as representative methods that illustrate the spirit of the invention. These examples are not to be construed as limiting the scope of this invention as other equivalent means will be readily apparent to those skilled in the art in the light of the disclosure, the figures and the claims.

DESCRIPTION OF INVENTIVE EMBODIMENTS

EXAMPLE I

Preparation of hemoglobin solution: The starting material was 5 units of out-dated human blood that contained anti-coagulant acid-citrate-dextrose solution. The blood was obtained from a local blood bank. First the blood was poured from the blood bank bags into autoclaved 500 ml centrifuge tubes. The tubes were capped and the blood, comprised of erythrocytes, leucocytes, platelets, and plasma was centrifuged at 5,000 rpm (4000g) for 30 minutes at 4° C. Then, the plasma and buffy coat containing the leucocytes and platelets were removed by suction through a sterile pipette and discarded. The sedimented erythrocytes which remained were washed four times by suspending in approximately three times their volume in ice-cold sterile 0.9% physiological saline or 1.6% sodium chloride solution. Following each wash, the cells were resedimented by centrigfugation and the supernatent removed and discarded. Next, the washed red cells were lysed with either an equal volume of ice-cold water or hypertonic, 0.05 M phosphate buffer, pH 7.2, to rupture the intact cell wall and free the hemoglobin. Lysis was completed by vigorously shaking the cellular water suspension for 1 to 2 minutes at room temperature. Then, the lysed cells were placed in a sterile 2 liter separatory funnel, the total volume of the solution was approximately 1,500 ml. The lysed erythrocyte-water mixture was freed of stroma by extraction with 350 ml. of ice-cold reagent-grade toluene. Extraction was carried out by shaking in the funnel for at least 5 minutes.

After setting overnight at 4° C, the extraction mixture separates into three layers: an upper layer of toluene containing stroma and lipids; a middle layer of cellular debris; and a lower layer of dark red aqueous hemoglobin solution. The lower hemoglobin layer, 800 to 1200 ml, was separated and centrifuged at 19,000 rpm (50,000g) for 60 minutes at 4° C to sediment any remaining cell debris. If, after the toluene extraction, no separation of the layers occurs, the toluene-water cellular emulsion was broken by either centrifugation at 5,000 rpm (4000g) for thirty minutes at 4° C, or by treating the emulsion with 0.15 volumes of Celite -535 filtrant, a diatomaceous earth filter. The aqueous hemoglobin solution was removed from the Celite by vacuum filtration and centrifuging at 19,000 rpm (50,000g). Any last trace of stroma in the hemoglobin was removed by either filtering through filters of pore size 0.22 $\mu$ or by passage through a 1½ inch layer of wet-packed Celite -535 filtrant, that was previously acid-washed, then washed with sterile pyrogen-free water. Next, the freshly prepared stromal-free hemoglobin solution was dialyzed against 0.05 M phosphate buffer, pH 7.6 using a Dow biofiber — 50 miniplant dialyzer. The hollow semipermeable cellulosic fibers of the dialyzer were first washed with 2.5% formalin and then rinsed with sterile pyrogen-free water to prevent possible bacterial contamination of the hemoglobin. The outside of the dialysis hollow fibers was flushed with sterile water and sterile phosphate buffer. Then, the hemoglobin solution was passed through the fibers at a flow rate of 20 ml per minute while the buffer was passed around the outside of the fibers, the buffer flowed in the opposite direction of the hemoglobin at a rate of 100 ml per minute. The hemoglobin solution was repeatedly passed through the fibers, at least three times, to insure complete electrolyte exchange and removal of cellular potassium ion. The hemoglobin solution was further clarified and made sterile by pressure filtration through a 0.22 $\mu$ filter comprised of mixed esters of cellulose, commercially available from Millipore Corporation. The stromal-free hemoglobin solution was analyzed to determine if it was stromal-free by adding about 1 ml of ice-cold saturated ammonium sulfate dropwise to 1 ml of hemoglobin solution with constant stirring. The absence of a precipitate indicated a stromal-free solution. The hemoglobin solution was stored at 4° to 6° C until needed.

The hemoglobin solution was analyzed to determine the amount of methemoglobin and total hemoglobin in the preparation. In oxyhemoglobin, the iron of the heme group is divalent; when hemoglobin is oxidized to methemoglobin, the iron is present in the trivalent state. As methemoglobin is unable to transport ligands such as CO, $O_2$ and NO, its presence in significant amounts is undesirable in the hemoglobin preparation. The presence of methemoglobin was determined spectrophotometrically by the cyanomethemoglobin method modified from the procedure in *Hawk's Physiological Chemistry*, page 1096, 1968. The hemoglobin and methemoglobin concentrations of the hemoglobin solution were determined as follows: first, the hemoglobin solution was diluted to a concentration of approximately 10 mg/ml (Solution A) and the solution absorbance measured at 630 nm against water ($L_1$). One drop of a KCN solution (1 part 10% KCN and 1 part 0.05 M phosphate, pH 7.6) was added and the solution mixed. This addition converts any methemoglobin present to cyanomethemoglobin. After two minutes the solution absorbance was again read at 630 nm against distilled water ($L_2$). Cyanomethemoglobin does not absorb at 630 nm. Then, 1 ml of solution A was diluted with 9 ml of distilled water. One drop of 20% potassium ferricyanide was added and after 2 minutes, one drop of 10% KCN was added. The solution was mixed and its absorbance read at 540 nm against a blank consisting of 10 ml of water, containing one drop each of 20% potassium ferricyanide and 10% KCN ($L_3$). The concentration of methemoglobin and hemoglobin were calculated as follows:

Concentration of methemoglobin (mM) = ($L_1$ − $L_2$)/3.7 × dilution factor solution A, ($\epsilon mM$=3.7 for methemoglobin at 630 nm). Total concentration of hemoglobin ($mM$) = $L_3$11.0 × dilution factor of solution A × 10, ($\epsilon mM$=11.0 for cyanomethemoglobin at 540 nm). The results for freshly prepared hemoglobin were 0 to 0.3% (w/v) methemoglobin, while the total hemoglobin concentration was usually 13 to 14% (w/v) or 130 to 140 mg of hemoglobin per ml.

The oxidation of hemoglobin to methemoglobin for determining the millimolar extinction coefficient at wavelength of maximum absorbance was done by reacting hemoglobin with potassium ferricyanide, with the latter present in a stoichiometric amount plus a 5% excess based on heme equivalent. Any excess of low molecular weight reagents was removed by dialysis against 0.2 M phosphate buffer having a pH of 6.8 followed by dialysis against glass-distilled water according to the method described in *science*, Vol. 144, page 68, 1968.

For determining the millimolar extinction coefficients, the iron content of the sample was determined by atomic absorption spectroscopy according to the procedure in *Am. J. Clin. Path.*, Vol. 48, pages 225 to 228, 1967, and the modification reported in *The Physiologist*, Vol. 15, page 138, 1972. With the modification, a 0.007% solution of albumin is added to the reference iron standards to balance the protein concentration in standards and samples.

From the absorbance of the solution at a wavelength of maximum absorbance, λ, and the iron content of the sample, the extinction coefficients are calculated according to the following formula:

$$\epsilon = \frac{\text{Absorbance at } \lambda \text{ max}}{\text{mole Fe}}$$

Using the reported procedures, the hemoglobin prepared according to Example I when oxidized to methemoglobin, gave an $\epsilon = 3.7 \times 10^3$ at 630 nm, and when cyanide was added, an $\epsilon = 11.1 \times 10^3$ at 540 nm. The spectral properties of hemoglobin and polyhemoglobin in either the methemoglobin or cyanomethemoglobin form are reported for various examples in accompanying Table 2.

Cross-linking of hemoglobin as oxyhemoglobin, deoxyhemoglobin and carbonmonoxyhemoglobin was carried out in like manner except that the atmosphere of the reaction vessel was made to correspond to the form of hemoglobin present. The cross-linking of deoxyhemoglobin was performed with oxygen-free solvents, prepared by boiling the solvent under an inert gas and storing under an inert atmosphere. The polymerization described in the examples below are not intended to limit the invention to that ligand form of hemoglobin, as cross-linking will occur independent of the ligand state.

EXAMPLE II

Reaction of deoxyhemoglobin with glutaraldehyde: to a 1 liter flask equilibrated with argon at about 4° C was anaerobically added 250 ml of deoxyhemoglobin solution, 14.2% w/v in 0.05 M phosphate buffer, with a pH of 7.1 and a methemoglobin content of less than 0.3% w/v. The solution was kept anaerobic by continuous flushing with nitrogen. Then, 4.65 ml of 1.3 M lysine monohydrochloride in deaerated 0.05 M phosphate buffer was added and the solution equilibrated with nitrogen for 18 hours to remove any possible air contamination.

Next, 5 ml of 25% aqueous glutaraldehyde was diluted to 125 ml with deoxygenated 0.05 M phosphate buffer to give a 0.1 M glutaraldehyde solution, pH 7.6; and 121 ml of this solution was added to the deoxyhemoglobin lysine solution. The resulting solution was stirred for 3 to 18 hours under the reaction conditions described above to ensure cross-linking of the deoxyhemoglobin. The cross-linking reaction was quenched by adding 46.5 ml of deaerated lysine solution, 1.3 M, and the solution stirred an additional 18 hours.

After quenching, the reaction solution was oxygenated with 100% oxygen and the solution clarified by centrifuging and filtering through a 0.65 micron Millipore filter. These steps and all subsequent steps were performed without allowing the temperature of the solution to exceed 15° C. The clarified solution was dialyzed against an appropriate electrolyte solution to remove unbound glutaraldehyde and excess lysine. The total volume after dialysis was 350 ml, with a pH of 6.77 at 37° C in normal physiological saline.

Optionally, cations and other components can be added to the polyhemoglobin solution at this step of the procedure. Also, the pH can be adjusted to the pH of the environment of use and the solution can be sterilized by filtering through an autoclaved filteration unit holding a filter with a pore size of about 0.22 $\mu$.

Figure 1:
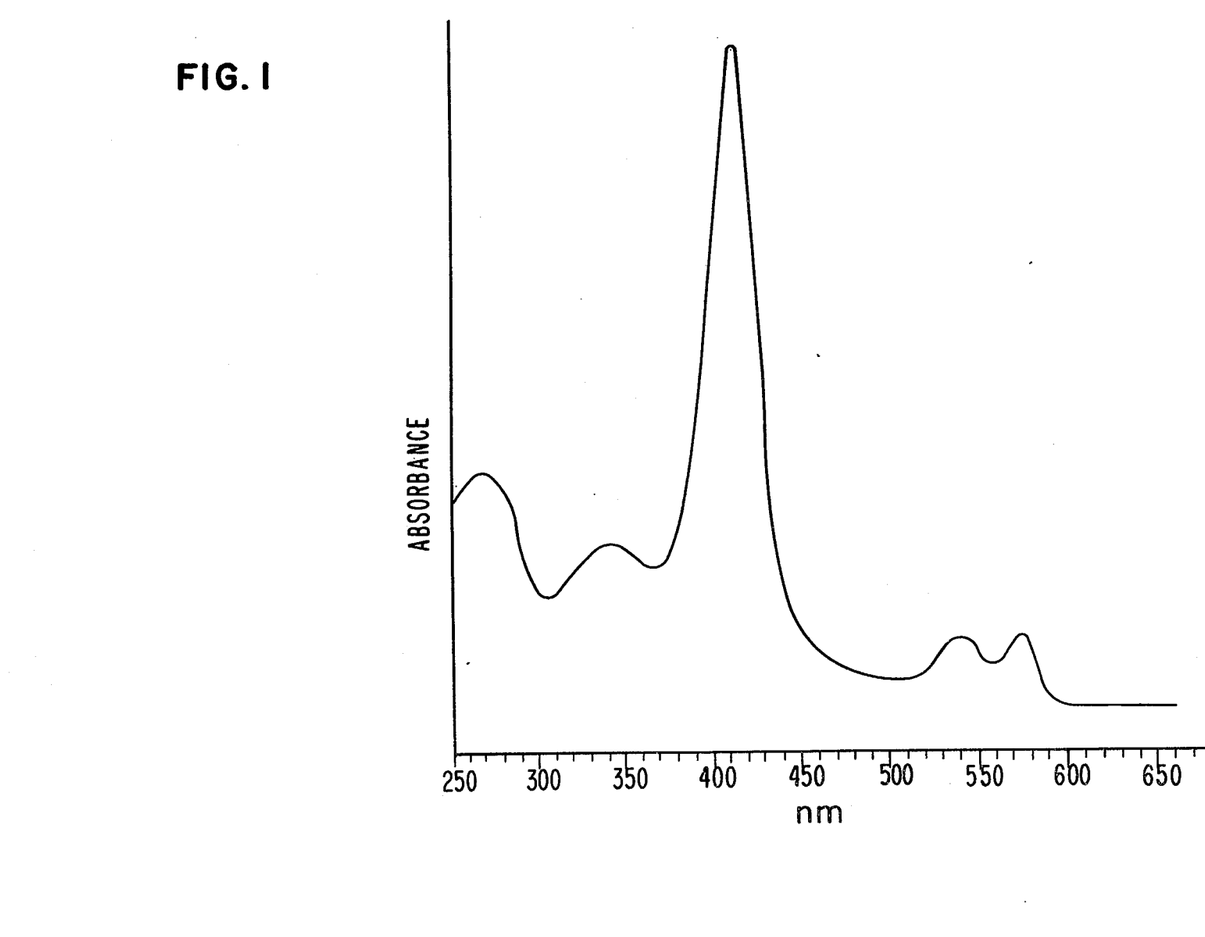
Figure 2:
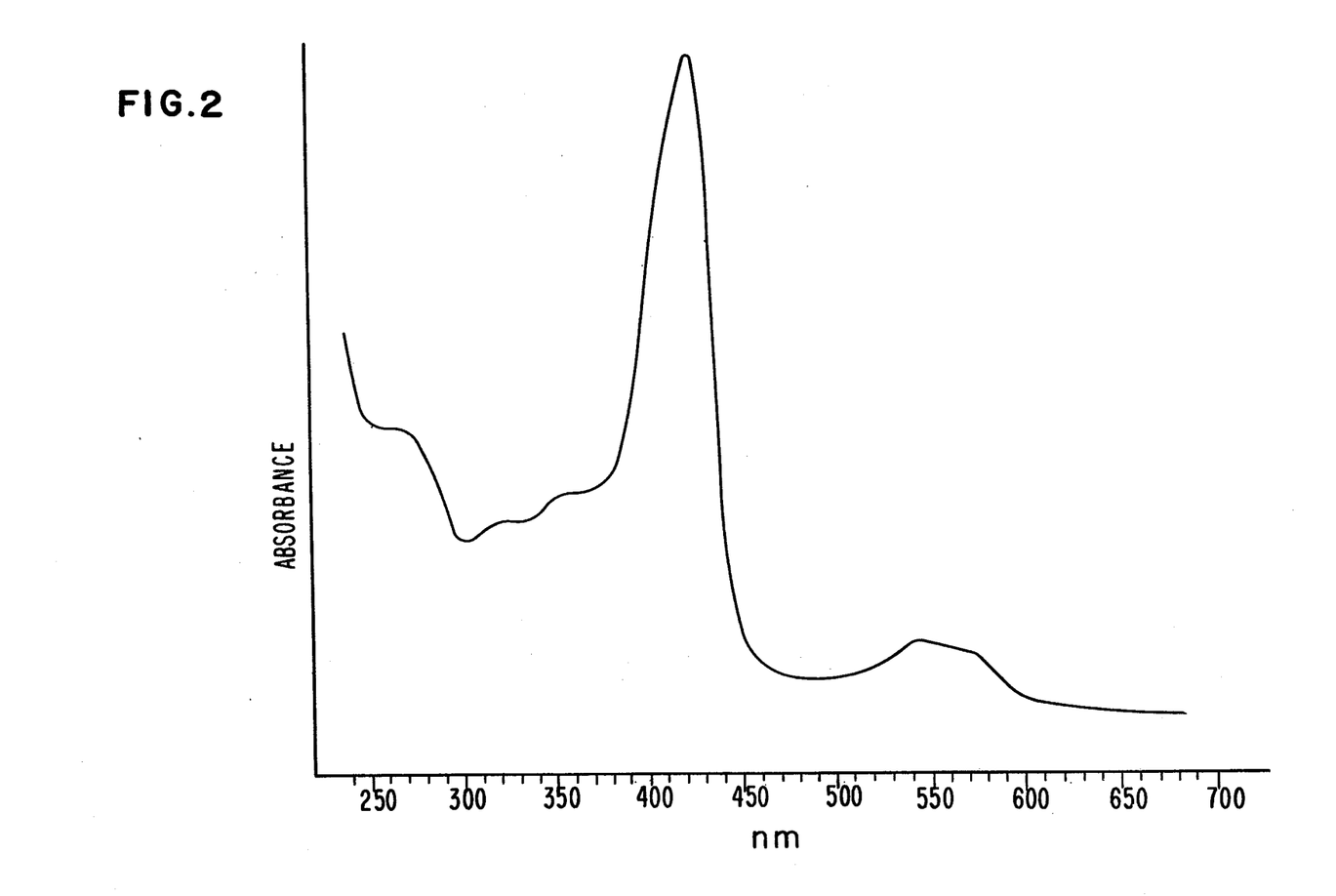

Spectral analysis of the solution in the ultraviolet and visible region gave the absorption curve as shown in FIG. 1. Spectral analysis of the deoxygenated polymerized hemoglobin obtained by solution equilibration with nitrogen showed the curve in FIG. 2. Molar extinction coefficients for polymethemoglobin and polycyanomethemoglobin prepared by oxidation of the polyhemoglobin with potassium ferricyanide according to Example I were determined and the results are reported in accompanying Table 2.

Analysis for intermolecular cross-linking between hemoglobin tetramers was done by gel filtration using a biologically inert polyacrylamide having a molecular weight exclusion limit of 150,000 daltons. The eluted material was monitored at 546 nm. The resulting elution profile showed that the reaction conditions employed produced over 90% macromolecular weight hemoglobin, since the majority (>90%) of the eluted protein was excluded from the gel pores. The polyacrylamide gel is commercially available as Bio-Gel P-150 from Bio-Rad Laboratories, Richmond, California. Procedures for using the gel are described in Gel Chromatography, pages 30 to 35, June 1971, published by Bio-Rad, see supra; and in J. Pure Appl. Chem., Vol. 6, 233, 1963; J. Biol. Chem., Vol. 244, 4985, 1969; ibid, Vol. 245, 5161, 1970; ibid, Vol. 245, 5166, 1970; Biochim. Biophys. Acta, Vol. 214, 463, 1970; and Anal. Biochem., Vol. 32, 522, 1969.

Further evidence of covalent cross-linking was obtained by dodecyl sulfate-polyacrylamide gel electrophoresis. The procedure used is described in J. Biol. Chem., Vol. 244, pages 4406 to 4412, 1969. The procedure involves denaturing the polymerized hemoglobin in sodium dodecyl sulfate to break all non-covalent interactions in the protein. Following denaturation, electrophoresis through polyacrylamide gel separates the covalently cross-linked aggregates on the basis of molecular size. The result of this analysis showed deoxyhemoglobin polymerized with glutaraldehyde to consist of covalently cross-linked aggregates ranging in molecular weights corresponding to integral multiples of the monomer, $1 < n < 8$.

The molecular weight of the polymerized hemoglobin was determined by gel permeation chromatography. Procedures for molecular weight determinations are described in Biochim. Biophys. Acta, Vol. 79, pages 393 to 398, 1964; ibid, Vol. 79, pages 399 to 406, 1964; Nature, Vol. 220, pages 1125 to 1127, 1 FEBS Letters, Vol. 2, pages 242 to 244, 1969; Anal. Chem., Vol. 35, pages 1950 to 1953, 1963; Science, Vol. 141, pages 13 to 20, 1963; Biochim. Biophys. Acta, Vol. 214, pages 463 to 467, 1970; and J. Biol. Chem., Vol. 125, pages 37 to 44, 1938.

Gel permeation through agarose gel was used for molecular weight determination. The agarose gel has a molecular weight exclusion limit of $20 \times 10^6$ daltons. The spherical agarose gel beads are available as Sepharose®4-B from Pharmacia Fine Chemicals, Uppsala, Sweden. Elution through a column, calibrated with globular proteins, gave the number average molecular weight, $\overline{M}_N$, the weight average molecular weight, $\overline{M}_w$, and degree of polymerization, D.P., for the polymerized hemoglobin. These results are seen on Table 1.

Figure 4:
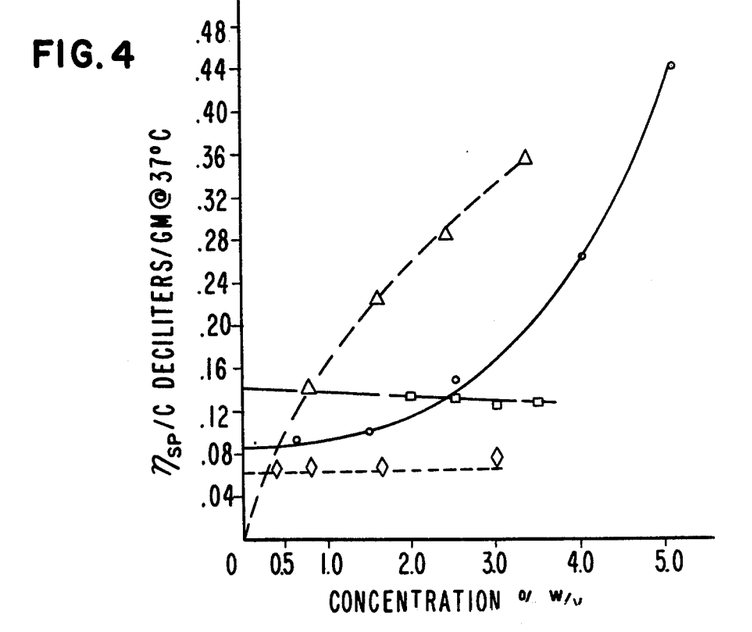

Further polyhemoglobin characterization was obtained from viscosity and osmolarity measurements. The results showed an increased viscosity for deoxyhemoglobin cross-linked with glutaraldehyde, relative to hemoglobin, and also showed Newtonian behavior indicating the independence of viscosity on the rate of shear. This polymer showed a high increase of relative viscosity with concentration, as seen in FIG. 4 and illustrated by the line having the circles. The viscosity data were measured with an Ostwald viscometer, number 25, at 37° C, according to the ASTM designation: D2162-64 protocol. Osmolarity was measured with a vapor pressure osmometer, Model 302B, Hewlett Packard, calibrated using the advanced freezing point standards NaCl. The polymerized hemoglobin solutions in a physiological carrier were all iso-osmotic, 300 mOsm/Kg $H_2O$ ($\pm 10\%$) with an intrinsic viscosity $[\eta] = 0.091$ deciliters/gram.

The degree of cationic binding to polyhemoglobin was determined by adding either calcium ion or magnesium ion to the solution. The samples were incubated at 4° C for 15 minutes to 18 hours and the macro-molecular hemoglobin separated from the solvent by centrifugation through a membrane ultrafilter with a molecular weight retention limit of 50,000. These ultrafilters are sold as Centriflo Membrane Ultrafilters from Amicon Corporation, Lexington, Massachusetts. The clear filtrate was analyzed for calcium or magnesium content by using Calcium Rapid Stat and Magnesium Rapid Stat available from Pierce Chemical Co., Rockford, Illinois. The results showed no binding of calcium ion or magnesium ion to the polyhemoglobin.

The sterility of the solutions was determined by standard procedures for liquid media, USP XVIII, page 856 to 865, 1970. All samples passed through a 0.22 $\mu$ filter were found to be sterile.

Figure 3:
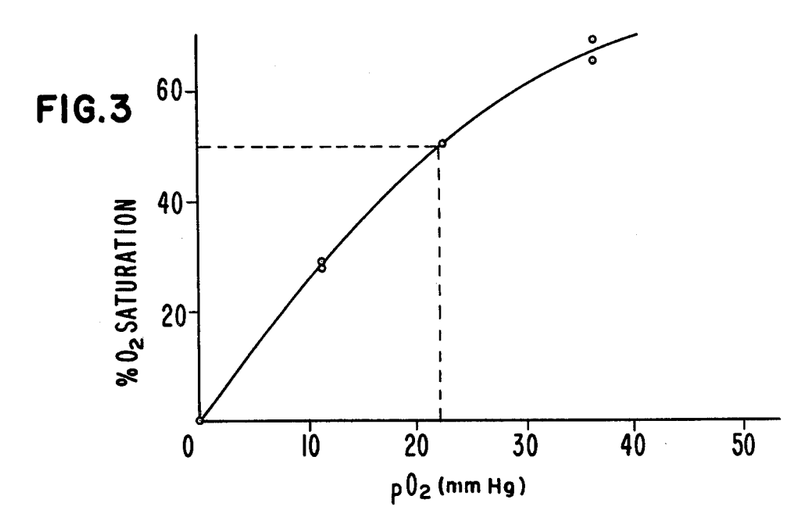

Analysis of polymerized hemoglobin for total hemoglobin and methemoglobin content by the procedure as described under Example I, gave a hemoglobin concentration of about 8% w/v and a methemoglobin concentration of less than 0.6% w/v, indicating that the hemoglobin iron is preserved in the divalent state. Oxygen binding capacity was measured in a Van Slyke apparatus according to the procedure in *J. Biol. Chem.*, Vol. 61, pages 523 to 573, 1924; and was found to be close to 100%. The oxygen affinity of the macro-molecular hemoglobin, measured as the partial pressure of oxygen required to half saturate the polyhemoglobin solution, was found as 22 mm Hg oxygen pressure or $P_{50} = 22$ mm Hg, at atmospheric pressure and 37° C, with the solution having a pH of 7.1. The oxygen dissociation curve is illustrated in FIG. 3.

The oxygen-dissociation curves of hemoglobin and its derivatives were determined by first equilibrating a hemoglobin sample by tonometry with a gas mixture of known composition and then spectrophotometrically measuring the equilibrated sample. The oxygen-dissociation curves for hemoglobin and its derivatives are also determined by taking hemoglobin that is tonometered and photometrically measuring it in an oxygen saturation meter. The procedure and tonometer used for these determinations are described in *Pflügers Archiv.*, Vol. 15, pages 418 to 424, 1960; *Operators Manual — 137 Tonometer*, pages 1 to 14 and 37 to 42, 1965, published by Instrumentation Laboratory, Inc., Lexington, Massachusetts; and *J. Appl. Physiol.*, Vol. 28, pages 227 to 233, 1970. The oxygen saturation procedures are known to the art in *Scan. J. Clin. Lab. Inv.*, Vol. 14, pages 587 to 597, 1962, and in *Oxygen Saturation*, pages A1 to A3, C1 to C3 and E1 to E4, 1968, published by Radiometer, Copenhagen, Denmark.

EXAMPLE III

Reaction of oxyhemoglobin with glutaraldehyde: the polymerization of oxyhemoblobin with glutaraldehyde was carried out by repeating the procedure of Example II with all conditions as set forth except that the solutions and the reaction environment are kept aerobic by equilibration with either air or 100% $O_2$. Optionally, the polymerized oxyhemoglobin solution can be sterilized by filtering through a 0.45 $\mu$ filter.

Analysis of intermolecular cross-linking was done by gel filtration, as in Example II, and the resulting elution profile showed that the reaction resulted in 90% macro-molecular hemoglobin. The results of the molecular weight analysis are shown in Table 1. The macromolecular oxyhemoglobin solution was iso-osmotic, 300 mOs/Kg $H_2O$, ($\pm 10\%$) with an intrinsic viscosity $[\eta] = 0.110$ deciliters per gram. This polymer showed a high increase of relative viscosity with concentration as illustrated in FIG. 4 by the curve having triangles.

Figure 5:
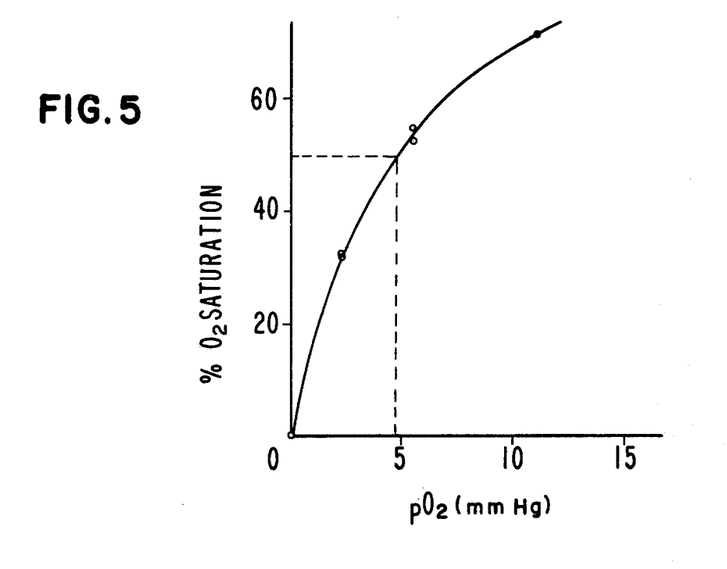

Analysis of the polyhemoglobin for total hemoglobin and methemoglobin showed a hemoglobin concentration of about 8% w/v and a methemoglobin concentration of less than 0.6% w/v. The oxygen capacity was found to be close to 100%, the $P_{50}$ was 4 mm Hg oxygen pressure, at atmospheric pressure and 37° C, with the solution having a pH of 7.1, and having an oxygen dissociation curve as seen in FIG. 5.

EXAMPLE IV

Reaction of deoxyhemoglobin with divinylsulfone: to a 1 liter flask equilibrated with argon at about 4° C was anaerobically added 250 ml of deoxyhemoglobin solution, 14% w/v in 0.05 M phosphate buffer, with a pH of 7.1 and a methemoglobin content of less than 0.3% w/v. The solution was kept anaerobic by continuous flushing with moist nitrogen. The deoxyhemoglobin solution was then equilibrated with nitrogen for 18 hours to remove any possible air contamination.

Next, 115 mg (0.85 ml) of divinyl sulfone was added and the reaction solution stirred at 4° C for 72 to 96 hours. Every twenty-four hours, the pH of a small aliquot, about 0.5 cc, of the reaction solution was measured and the progress of the reaction was determined by gelfiltration through Bio-Gel P-150 as previously described. If necessary, the pH was adjusted to approximately 7.2 to 7.4 with 1N NaOH. When gel filtration showed that approximately 80 to 90% of the red material was excluded from the gel, that is, $M_{tc} > 150,000$ daltons, the reaction solution was quenched by the addition of 30 ml of deaerated 1.3 M lysine solution to deactivate unreacted vinyl groups. Then, the reaction solution is kept anaerobic and stirred for an additional 18 hours.

After quenching, the reaction solution was oxygenated with 100% oxygen and the solution clarified by centrifuging and filtering through a 0.65 micron Millipore filter. These steps and all subsequent steps were performed without allowing the temperature to exceed 15° C. The clarified solution was then dialyzed against an electrolyte to remove unbound divinyl sulfone and excess lysine. The total volume after dialysis was 280 ml, with a pH of 6.92 at 37° C in physiological saline. The macro-molecular hemoglobin solution was mixed with a physiological vehicle, the pH adjusted to the physiologically acceptable range, as described in Example II, and the solution sterilized by filtering through a Millipore filter with a pore size of 0.22 microns.

Figure 6:
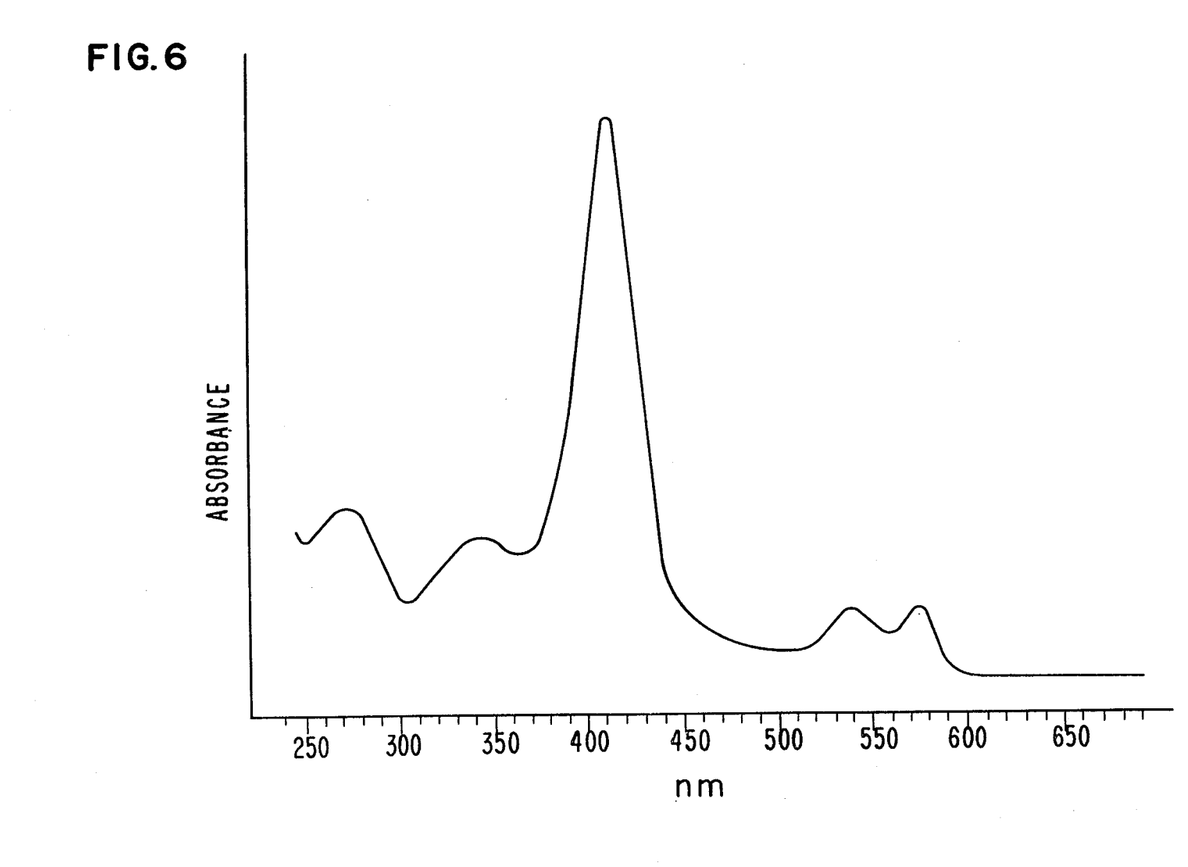
Figure 7:
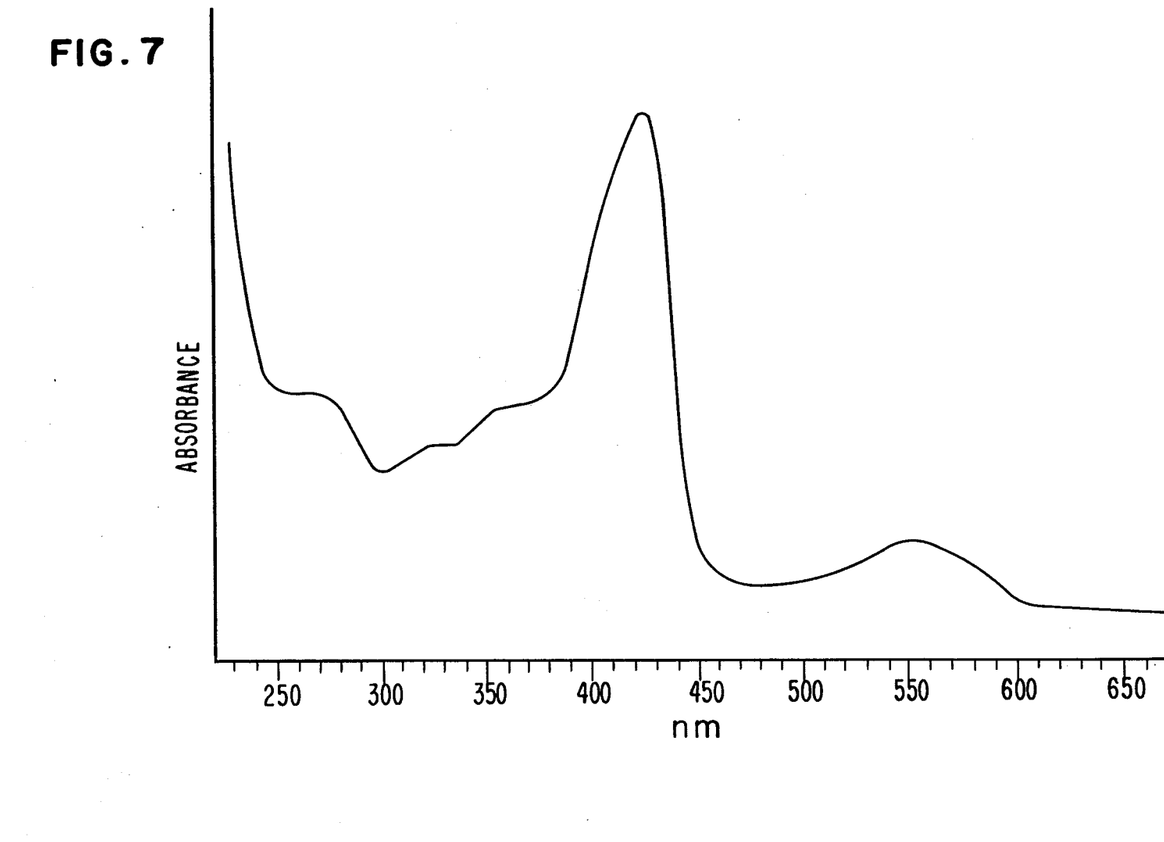

The percent conversion of hemoglobin to macromolecular hemoglobin was determined by gel filtration, and evidence of covalent cross-linking was obtained from polyacrylamide gel electrophoresis using sodium dodecyl sulfate as described in Example II. Similar results were found for deoxyhemoglobin cross-linked wth divinyl sulfone as were found for deoxyhemoglobin cross-linked with glutaraldehyde and described in Example II. Spectral analysis of the oxygenated solution in the ultraviolet and visible region showed the absorption spectrum as seen in FIG. 6. Spectral analysis of the deoxygenated macro-molecular hemoglobin solution, deoxygenated by equilibration with nitrogen, showed the spectrum in FIG. 7. The results of the molar extinction coefficient determination is reported in Table 2.

TABLE 1
MOLECULAR WEIGHT OF POLYMERIZED HEMOGLOBIN

| POLYMERIZED Hb | METHOD+ | $\overline{M}_w$ (×10⁻⁵) | $\overline{M}_N$ (×10⁻⁵) | D.P. | $\overline{M}_{visc}$ (×10⁻⁵) |
|---|---|---|---|---|---|
| Example II  | 1 | 5.3 (±.8)   | .9 (±.1)  | 5.6 (±.6) | —   |
|             | 2 | —           | —         | —         | 1.6 |
| Example III | 1 | 11.2 (±1.1) | 1.6 (±.3) | 9.6 (±1.8)| —   |
|             | 2 | —           | —         | —         | 1.8 |
| Example IV  | 1 | 5.9 (±1.8)  | 1.1 (±.1) | 6.8 (±.6) | —   |
|             | 2 | —           | —         | —         | 2.3 |
| Example V   | 1 | 5.0 (±1.4)  | .95 (±.1) | 6.0 (±.6) | —   |
|             | 2 | —           | —         | —         | 1.0 |

+Method used:
(1) GPC-Sepharose®4B
(2) Viscosity

Hb is the accepted symbol for hemoglobin, $\overline{M}_w$ is weight average molecular weight, $\overline{M}_n$ is number average molecular weight, D.P. is degree of polymerization, and $\overline{M}_{visc}$ is viscosity average molecular weight.

TABLE 2
SPECTRAL PROPERTIES OF HEMOGLOBIN AND POLYMERIZED HEMOGLOBIN

| EXAMPLE | Hb or Poly(Hb)$_n$ | FORM | λ | $\epsilon \times 10^{-3}$ |
|---|---|---|---|---|
| I  | Hb         | M | 630 | 3.7  |
| I  | Hb         | C | 540 | 11.1 |
| II | Poly(Hb)$_n$ | M | 630 | 3.9  |
| II | Poly(Hb)$_n$ | C | 540 | 9.7  |
| IV | Poly       | C | 540 | 9.4  |
| V  | Poly       | M | 630 | 3.2  |
| V  | Poly       | C | 540 | 9.7  |

In the table, Hb is the abbreviation for hemoglobin, Poly(Hb)$_n$ denotes polymerized hemoglobin, M is methemoglobin, C is cyanomethemoglobin, λ is wavelength and ε is the molar extinction coefficient.

Figure 8:
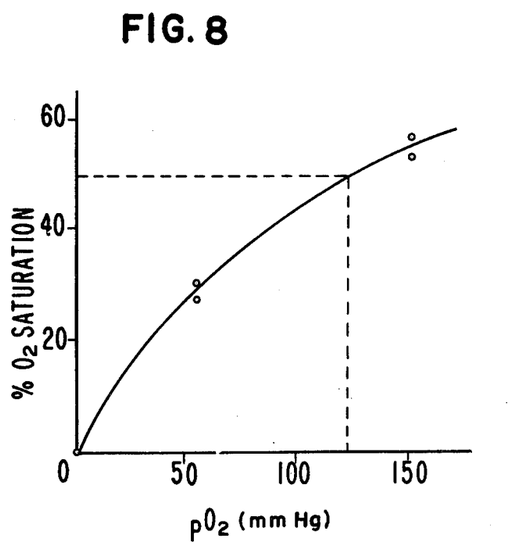

The results of the molecular weight determinations utilizing gel permeation chromatography and viscosity methods are shown in Table 1. The polyhemoglobin solution in a physiological carrier was iso-osmotic, 300 mOsm/Kg H$_2$O (±10%), with an intrinsic viscosity [η] = 0.139 deciliters per gram. The relative viscosity was essentially independent of concentration as shown in FIG. 4, with this polymer represented by the lines having squares. Analysis of the macro-molecular hemoglobin for total hemoglobin and methemoglobin gave a hemoglobin concentration of about 8.5% w/v and a methemoglobin concentration of less than 0.4% w/v. The oxygen capacity was found to be approximately 100% with a P$_{50}$ value of 100–120 mm Hg oxygen pressure, at atmospheric pressure and at 37° C, with the solution having a pH of 6.9 and an oxygen dissociation curve as shown in FIG. 8.

EXAMPLE V

Reaction of oxyhemoglobin with divinyl sulfone: the procedure for the oxyhemoglobin reaction with divinyl sulfone was as given in Example IV except that all solutions and the reaction environment were kept aerobic by equilibration with either air or 100% O$_2$. The time required for the reaction to be complete, as ascertained from elution through Bio-Gel P-150, was about 96 hours.

Figure 9:
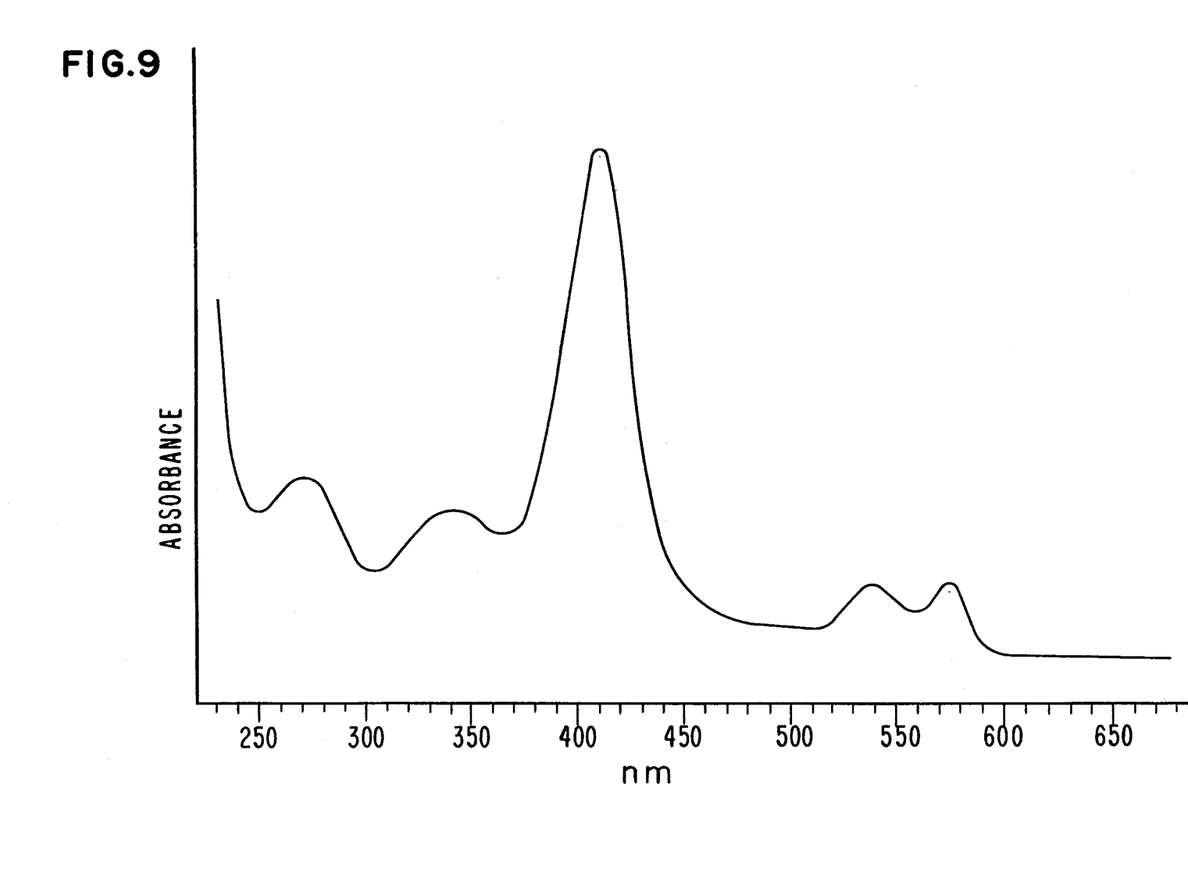

Conversion to macro-molecular weight hemoglobin was determined by gel filtration and evidence of covalent cross-linking was obtained from polyacrylamide gel electrophoresis using sodium dodecyl sulfate as described under Example II. Similar results were found for oxyhemoglobin cross-linked with divinyl sulfone as were found for deoxyhemoglobin cross-linked with either glutaraldehyde or divinyl sulfone as described in Examples II and IV. Spectral analysis of the oxygenated solution in the ultraviolet and visible region showed the absorption spectrum as seen in FIG. 9. The results of the molecular weight determinations using gel permeation chromatography and viscosity methods are shown in Table 1. In Table 2, the extinction coefficients are reported for polyhemoglobin in the methemoglobin and cyanomethemoglobin form.

Figure 10:
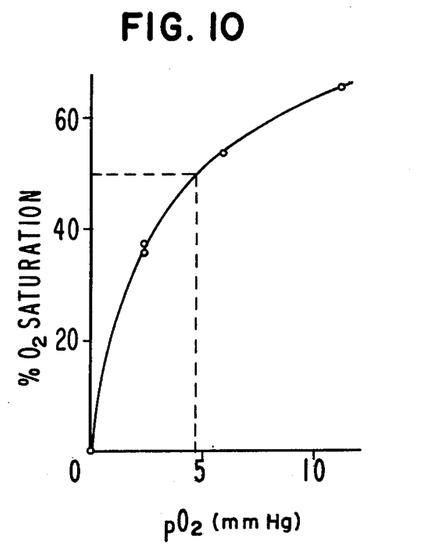

The cross-linked oxyhemoglobin solution in a physiological carrier was iso-osmotic, 300 mOsm/Kg H$_2$O (±10%) with an intrinsic viscosity [η] = 0.061 deciliters per gram. The relative viscosity was essentially independent of concentration as shown in FIG. 4, with this polymer represented by diamonds. Analysis of the macro-molecular oxyhemoglobin for total hemoglobin and methemoglobin gave a hemoglobin concentration of about 8.5% w/v and a methemoglobin concentration of less than 0.4% w/v. The oxygen capacity was found to be close to 100% and the P$_{50}$ was found to be 4 mm Hg oxygen pressure, at atmospheric pressure and at 37° C, with the solution having a pH of 6.9 and an oxygen dissociation curve as shown in FIG. 10.

EXAMPLE VI

Reaction of deoxyhemoglobin with hexamethylene diisocyanate: into an argon equilibrated 100 ml round bottom flask at 4° C was anaerobically added 20 ml of deoxyhemoglobin solution, 12% (w/v) in 0.05 M phosphate buffer with a pH of 7.1, and the solution was kept anaerobic by continuous flushing with moist argon gas. The solution was held at this temperature and stirred under nitrogen for approximately 18 hours to remove any possible air contamination.

Next, 0.138 ml of hexamethylene diisocyanate was added to the deoxyhemoglobin and the reactants stirred under the conditions described above for 72 hours to cross-link the deoxyhemoglobin. Any excess hexamethylene diisocyanate remaining in the reaction mixture was inactivated by adding 4 ml of deaerated 1.3 M lysine solution followed by 18 hours of stirring to insure deactivation. The solution was oxygenated and clarified by centrifugation.

Conversion to polymerized hemoglobin was determined by gel filtration through Biogel P-150. The majority of the eluted material, 85%, was excluded from the pores of the gel indicating a protein molecular weight in excess of 150,000 daltons. Analysis of the polymerized deoxyhemoglobin for total hemoglobin and methemoglobin gave a hemoglobin concentration of about 9.5% (w/v) and a methemoglobin concentration of less than 0.7% w/v. The $P_{50}$ of the polymerized hemoglobin was found to be 3.5 mm Hg oxygen pressure at atmospheric pressure at 37° C, with the solution having a pH of 7.1.

EXAMPLE VII

Reaction of oxyhemoglobin with hexamethylene diisocyanate: the reaction of oxyhemoglobin with hexamethylene diisocyanate was carried out according to the procedure described in Example VI, with all conditions as described except the solution and the environment were kept aerobic by equilibration with air or oxygen. The percent conversion to polymerized oxyhemoglobin as determined by gel filtration, gave results consistent with those obtained in Example VI, for a yield of 85% macromolecular oxyhemoglobin.

EXAMPLE VIII

Reaction of deoxyhemoglobin with dimethylsuberimidate dihydrochloride: the cross-linking of deoxyhemoglobin was carried out as follows: into a 50 cc 3-necked round bottomed flask, flushed with argon and held at 5°–10° C, was first added 20 ml of deoxyhemoglobin, having a concentration of 13% w/v in 0.25 M phosphate buffer with a pH of 8.0 and a methemoglobin content of less than 0.3% w/v, followed by the addition of 263 mg of dimethylsuberimidate dihydrochloride dissolved in 4 ml of deaerated, saturated sodium bicarbonate solution to produce a reaction mixture. The pH of the mixture was adjusted to 8.0 with 1 N NaOH and held there with the addition of 1 M $NaH_2PO_4$ until the pH did not change for about 15 minutes. The flask was stoppered and the reaction continued with stirring at 4° C for 1 hour. The flask was opened and allowed to equilibrate with air. The reaction was quenched by adding thereto 2 ml of 1.3 M lysine with the mixture stirred an additional 3 hours to insure a quenched reaction. Finally, the solution was clarified by centrifugation and then dialyzed against 0.05 M phosphate buffer at pH 7.6.

Conversion to polymerized hemoglobin was determined by gel filtration through Biogel P-150. The majority of the eluted material (90%) was excluded from the gel pores, indicating a molecular weight in excess of 150,000 daltons. Also, the macro-molecular deoxyhemoglobin had a hemoglobin concentration of about 8% and a methemoglobin concentration of less than 0.6% w/v. The $P_{50}$ of the polymerized hemoglobin was found to be 2.5 mm Hg oxygen pressure, at atmosphere pressure and at 20° C, with the solution having a pH of 7.35.

EXAMPLE IX

Reaction of oxyhemoglobin with dimethylsuberimidate dihydrochloride: The cross-linking of oxyhemoglobin with dimethylsuberimidate was carried out according to the procedure of Example VIII, with all the conditions as previously described, except that the solution and its environment were kept aerobic by equilibration with air. Physical analysis of the polymerized oxyhemoglobin showed results consistent with the cross-linked deoxyhemoglobin of Example VIII. The $P_{50}$ was 2.5 mm Hg oxygen pressure, at atmospheric pressure and 37° C, with the solution having a pH of 7.45.

EXAMPLE X

Polymerization of oxyhemoglobin with butadiene diepoxide: a 20 ml solution of oxyhemoglobin, 13.4% w/v in 0.05 M borate buffer with a pH of 8.0 and a methemoglobin content of less than 0.5% w/v was added to a flask containing 320 µl of butadiene diepoxide and 370 µl of triethylamine, both as neat liquids. The solution was stirred at 5° C for 96 hours under air and then the reaction quenched by the addition of 500 mg of solid cysteine. The solid was dissolved by stirring and allowed to react for 18 hours. Analysis for intermolecular cross-linking was done by gel filtration through Biogel P-150. The majority of the eluted material, 85%, was excluded from the gel indicating a molecular weight in excess of 150,000 daltons. Analysis of the polymerized oxyhemoglobin for total hemoglobin and methemoglobin gave a hemoglobin concentration of about 9.5% and a methemoglobin concentration of less than 0.4% w/v.

DESCRIPTION OF APPLICATION OF THE INVENTION

The cross-linked, stromal-free hemoglobins prepared according to the invention have a reversible ligand carrying property. That is, the polyhemoglobins possess the ability to become saturated with a ligand such as oxygen or carbon monoxide and to transport and release it to an environment of use or to a ligand receptor. This property makes polyhemoglobin useful as a blood substitute. The polyhemoglobin is soluble in aqueous media, blood, plasma, crystalloid solutions, buffered electrolyte solutions and colloid polymeric solutions. The polyhemoglobin has physiologically acceptable colloidal-osmotic properties which makes it useful as a blood plasma expander. Polyhemoglobin has a prolonged plasma survival time in vivo as seen by a half-life of more than twice that of non-polymerized hemoglobin, usually about 12 hours to 30 hours. Additionally, since the polyhemoglobin is stromal-free, deleterious effects on the renal system are prevented.

The polyhemoglobin's ability to transport and supply the ligand oxygen to vital tissues and organs in animals including domestic animals such as dogs and cats, for farm animals such as cows and pigs, to mammals, and in diverse ligand exchange uses, is seen in the tests set forth below. In this application and the accompanying tests, the terms and phrases used herein have the following meaning: the phrase "substantially stromal-free" means the polyhemoglobin does not contain any red cell stromal material including non-hemoglobin proteins, phospholipids and lipids. The term "half-life" means the period in time in which the initial amount of polyhemoglobin in an in vivo environment falls to half its initial value. The expression "dissociation curve" denotes the extent to which polyhemoglobin will bind or contain the ligand, for example oxygen, under ligand tension ranging from 0 mm Hg to 140 mm Hg. By "oxygen binding capacity" is meant the fraction, in percent, of the amount of oxygen which can combine with each heme group contained in polyhemoglobin. For example, 100% oxygen capacity means each heme contained in the polyhemoglobin can bind a maximum of one oxygen molecule. The term "oxygen affinity" refers to the $p_{50}$ value of polyhemoglobin, that is, the partial pressure, $pO_2$, of oxygen at 50% saturation. The phrase "blood substitute" denotes the property of the material to transport and supply oxygen to vital tissues and organs and to maintain intravascular oncotic pressure, and, by "plasma expander" is meant the ability of polyhemoglobin solutions to restore blood volume. The results of the above-mentioned test are set forth immediately below in Examples XI to XV.

EXAMPLE XI

The plasma residence time of polyhemoglobin was measured as follows: first, on the day before infusion, an indwelling catheter was placed in the saphenous vein on one hind leg of two dogs, and the blood volume of the dogs calculated by a standard technique. The calculated blood volume was based on the weight of the dog with the assumption that a dog's blood volume is about 7% of the dog's total body weight. Then, on the next day, 20% of the blood volume was withdrawn through the catheter and immediately replaced with the same volume of polyhemoglobin having a concentration of 7% in Ringer's solution. In a different dog, 20% of the blood volume was replaced with the same volume of native human hemoglobin. Native hemoglobin is isolated, non-crosslinked hemoglobin, having a concentration of 7% in Ringer's solution. Then, blood samples were taken from each dog at 2 hour intervals until the hemoglobin in the plasma decayed as determined spectophotometrically by the cyanomethemoglobin method described in Example I. The half-life of the polyhemoglobin and native hemoglobin was determined by a semi-logarithmic plot of time versus hemoglobin concentration in the plasma as this reduces any exponential decay processes to a linear response. The measured results showed the polyhemoglobins prepared according to the procedures in Examples II to V had a 2 to 8 fold increase in plasma residence time relative to native hemoglobin, which showed a 4 hour half-life residence time in the plasma of a dog.

EXAMPLE XII

The increased residence time of deoxyhemoglobin cross-linked with glutaraldehyde as in Example II, and hemoglobin was measured in male rats weighing 250 to 300 grams having one femoral vein cannulated for infusion, and one femoral artery cannulated for taking samples according to the procedure of Example XI. Additionally, in this example, the blood volume of the rat was calculated at 8% of the total body weight and the polyhemoglobin had a concentration of 8% in normal saline. The blood samples, 0.3 ml, were centrifuged at 500g to sediment cells. The plasma, containing polyhemoglobin, was analyzed for polyhemoglobin concentration by the cyanomethemoglobin spectral method of Example I. The results showed hemoglobin had a half-life residence time in plasma of 90 minutes, while the polyhemoglobin had a prolonged half-life residence time in rat plasma of 315 minutes.

EXAMPLE XIII

The total perfusion of rats with polyhemoglobin was carried out as follows: first, conventional male white laboratory rats weighing 250 to 300 grams were anaesthetized with 40 mg/kg of sodium pentobarbital. Then, both femoral arteries and one femoral vein were cannulated and the rats were heparinized. Throughout the studies, the rat's mean arterial pressure was continuously recorded via one femoral artery, and the other artery used to withdraw blood. The femoral vein was used for infusing polyhemoglobin.

The initial hematocrit was determined and 2 ml of blood withdrawn. Next, 2 ml of polymerized hemoglobin prepared according to Example II was infused into the rat over 2 to 3 minutes. Then, at 5 minute intervals, 1 ml of blood was withdrawn and 1 ml of polyhemoglobin infused into the rats and the perfusion continued until the rat's total blood volume, estimated at 8% of its body weight, was withdrawn. If the animals showed signs of shock, as seen by erratic respiration or a decreased arterial pressure, the time between blood withdrawals was extended, but the polyhemoglobin infusion rate of 1 ml every 5 minutes was continued to maintain the animals. A hematocrit was taken every 15 to 20 minutes and the hemorrhage and infusion continued until the hematocrit dropped from 45% to less than 5%. Throughout the experiments, the rat's skin appeared normal and there did not appear to be any leakage of polyhemoglobin into the extracellular fluids, as when the blood volume was replaced with a non-polymerized hemoglobin solution in glucose saline. The results indicated the polyhemoglobin delivered oxygen to tissues without diffusion into the extracellular fluid.

EXAMPLE XIV

Polyhemoglobin's ability to supply oxygen to animal tissues was seen in an isolated perfused rabbit heart septum assay performed as follows: first, the heart was removed from an anesthetized and heparinized rabbit and the septal artery cannulated and extraneous muscle cut away. Perfusion with canine erythrocytes in a glucose physiological saline solution was started as soon as the heart was removed to prevent possible tissue damage. Then, the septum was mounted in its frame so the heart beat and rate of change in tension could be measured. Oxygen consumption of the septa was varied by changing the heart rate, perfusate flow rate and temperature of the septa. Experimental conditions which produced maximum oxygen consumption of the septa without the concomitant loss of septal stability were determined by using canine erythrocytes as the perfusate. The arterial venous oxygen content was measured with a standard oxygen measuring instrument and the change in hemoglobin saturation from the arterial to venous flow was measured with the oxygen saturation meter described in Example II.

The results of the perfusion measurements with the polyhemoglobin as set forth in Examples II through V, showed that oxygen saturation decreased 50 to 70% and oxygen content decreased 3 volumes percent between the arterial and venous side of the septum, indicating polyhemoglobin in the perfused in vivo system provide oxygen to vital tissues. A general procedure for perfusion in isolated septa is described in *J. General Physiology*, Vol. 52, pages 682 to 691, 1968.

EXAMPLE XV

The use of polyhemoglobin for the management of hemorrhagic shock was carried out as follows: first, an animal was bled to a standard low blood pressure and the blood lost replaced by an equal volume of the blood substitute to be tested. Later, the animal again was bled and the relationship of the second to the first loss, expressed as the bleeding index, is $Bl_2/Bl_1 \times 100$. In this procedure, male rats were bled to a standard low blood pressure of 30 mm Hg and held there for 45 minutes by withdrawing blood to keep the pressure constant. At this time, the volume of blood withdrawn was noted giving $Bl_1$, and replaced with blood, saline, dextran, albumin, native hemoglobin or polyhemoglobin. The rats were left to recover for 3 hours, and then again blood was withdrawn to 30 mm Hg giving $Bl_2$, as described above. The results are shown in Table 3 and they indicate polymerized hemoglobin acts similar to whole blood according to this hemorrhage shock model. In the table, the substitutes are those polyhemoglobins prepared according to Examples II through V, with B indicates the rat's own blood, S indicating physiological saline, A is albumin, H is native hemoglobin, and D is dextran. Procedures for measuring the bleeding index are described in *Am. J. Physiol.*, Vol. 169, page 475, 1952 and *Am. J. Physiol.*, Vol. 173, page 403, 1953.

TABLE 3

| SUBSTITUTE | BLEEDING INDEX | ANIMALS |
|---|---|---|
| Example II | 100 ± 13 | 3 |
| Example III | 48 ± 15 | 4 |
| Example IV | 72 ± 23 | 5 |
| Example V | 75 ± 16 | 3 |
| B | 81 ± 13 | 24 |
| S | 27 ± 12 | 25 |
| A | 71 ± 9 | 3 |
| H | 36 ± 6 | 2 |
| D | 30 ± 11 | 17 |

The polyhemoglobin can be used as a blood plasma substitute, and blood plasma expander, mixed with a pharmaceutically acceptable carrier, or with other plasma substitutes and blood plasma expanders. The carriers can be crystalloids including physiological saline, a mixture consisting of saline and glucose, Ringer's solution, lactated Ringer's solution, Locke-Ringer's solution, Krebs-Ringer's solution, Hartmann's balanced saline, and heparinized sodium-citrate-citric acid-dextrose solution.

The polyhemoglobin can be mixed with water soluble physiologically acceptable polymeric plasma substitutes such as poly(ethylene oxide), polyacrylamide, polyvinyl pyrrolidone, polyvinyl alcohol, and ethylene oxide-polypropylene glycol condensates. Additionally, polyhemoglobin can be mixed with colloidal-like plasma substitutes and blood plasma expanders such as linear polysaccharides including dextrans having a molecular weight of 40,000 to 70,000, gum arabic pectins, balanced fluid gelatin, and hydroxyethyl starch. Generally, for the purpose of the invention, the polyhemoglobin is contained in a composition in about 1 to 10 percent, admixed with one of the above carriers or with a mixture thereof. The compositions are prepared by blending the agent in predetermined proportions to produce compositions. For example, a blood substitute solution comprising 5% polyhemoglobin in normal saline is prepared by adding 5 grams of polyhemoglobin to physiological saline, which is 0.85% sodium chloride in water, with q.s. to 100 ml. The polyhemoglobins are administered in the manner commonly employed in the blood transfusion art as disclosed in *Blood Transfusion*, by Hustis.

Other applications for polyhemoglobin include its use as an artificial oxygen exchange solution in conventional oxygenators, such as cardiac by-pass, extracorporeal circulatory assist devices, hollow-fiber and sheet-type membrane devices, used for assisting the circulation in ill patients. For these conditions, oxygenators are widely used to mechanically oxygenate venous blood extracorporeally. In operation, an oxygenator has one or more pumps for maintaining circulation and for perfusion of oxygen by the exchange of gases between blood in an isolated vascular bed and oxygen across an oxygenation membrane.

An oxygen exchange membrane is prepared according to the invention by saturating a porous synthetic semipermeable membrane, such as cellophane or a Millipore filter having a pore size of 0.45, 0.30 or 0.22 microns, a porosity of 75% and a thickness of 150 mm by soaking the membrane in an aqueous solution of polyhemoglobin to immobilize it within the micropores. The saturated membrane is next mounted in an oxygenator, equipped to a source of oxygen and having a gas flow meter to control the volumeric rate of oxygen delivered by the polyhemoglobin oxygenation membrane to blood in the vascular system.

The polyhemoglobin can be used as a source of protein and oxygen in the microbiological assay of foods for aerobic bacillus and staphylococus to insure the food is safe for animal and human consumption. The polyhemoglobin can be used for the storage and preservation of viable isolated perfused mammalian organs for their eventual transplant into a recipient, as a substitute for the oxygen-carrying capacity of red cells in mammals, and the polyhemoglobin can be used to supply oxygen as an aid in uranium leaching as disclosed in U.S. Pat. No. 3,003,848, and as a scavenger of noxious gases such as carbon monoxide and nitrogen oxygen and as a means for the purification of oxygen.

Having fully described the invention, it is to be understood that we do not wish to be limited to the details set forth, but the invention includes those embodiments obvious to those skilled in the art in the light of the present disclosure and claims.

We claim:

1. Polymerized, cross-linked, stromal-free hemoglobin, soluble in aqueous and physiological fluids, capable of reversibly binding a ligand, having a molecular weight of 64,000 to 1,000,000 and the formula poly$(Hb)_n$ wherein Hb is a member selected from the group consisting of a stromal-free monomer, dimer, trimer and tetramer hemoglobin, and $n$ is 4 to 60.

2. The polymerized hemoglobin according to claim 1 wherein the hemoglobin is deoxyhemoglobin.

3. The polymerized hemoglobin according to claim 1 wherein the hemoglobin is liganded hemoglobin.

4. The polymerized hemoglobin according to claim 1 wherein the polymerized hemoglobin is soluble in physiological fluids, has an oxygen capacity close to 100%, and an intrinsic viscosity of 0.04 to 0.16 deciliters per gram.

5. The polymerized hemoglobin according to claim 1 wherein the polymerized hemoglobin has a partial pressure at half-saturation, $P_{50}$, or 2.5 mm Hg to 120 mm Hg at 37° C and neutral pH.

6. The polymerized, cross-linked, stromal-free hemoglobin according to claim 1 wherein the hemoglobin is cross-linked with a member selected from the group consisting of gluturaldehyde, divinylsulfone, hexamethylene diisocyanate and butadiene diepoxide.

* * * * *